(12) United States Patent
Franke et al.

(10) Patent No.: US 6,534,070 B1
(45) Date of Patent: Mar. 18, 2003

(54) COMPOSITION WITH AZELAIC ACID

(75) Inventors: Patrick Franke, Berlin (DE); Clemens Günther, Berlin (DE); Jutta Riedl, Inzlingen (DE)

(73) Assignee: Schering Aktiengesellschaft, Berlin (DE)

( * ) Notice: Subject to any disclaimer, the term of this patent is extended or adjusted under 35 U.S.C. 154(b) by 0 days.

(21) Appl. No.: 09/554,738

(22) PCT Filed: Nov. 18, 1998

(86) PCT No.: PCT/EP98/07370

§ 371 (c)(1),
(2), (4) Date: Aug. 21, 2000

(87) PCT Pub. No.: WO99/25332

PCT Pub. Date: May 27, 1999

Related U.S. Application Data

(60) Provisional application No. 60/074,850, filed on Feb. 12, 1998.

(30) Foreign Application Priority Data

Nov. 19, 1997 (DE) .......................... 197 53 044
Feb. 20, 1998 (DE) .......................... 198 08 086

(51) Int. Cl.[7] .............. A61K 9/00; A61K 6/00; A61K 9/14; A61K 31/74; A61K 31/20; A61K 31/19

(52) U.S. Cl. ................ 424/401; 424/400; 424/486; 424/487; 424/78.02; 424/78.05; 514/557; 514/574; 514/859

(58) Field of Search .............. 424/400, 78.05, 424/401, 484, 486, 487, 78.02; 514/159, 557, 859, 574

(56) References Cited

U.S. PATENT DOCUMENTS 5,362,494 A * 11/1994 Zysman et al. ............. 424/401
5,618,522 A * 4/1997 Kaleta et al. ................. 424/60

FOREIGN PATENT DOCUMENTS

| EP | 336880 A2 | 3/1989 |
| EP | 696452 A1 | 2/1996 |
| WO | 95 04537 | 2/1995 |
| WO | 95 05163 | 2/1995 |
| WO | WO 95/11700 A2 | 5/1995 |
| WO | 96 05806 | 2/1996 |
| WO | 96 39119 | 12/1996 |

OTHER PUBLICATIONS

Grant & Hackh's Chemical Dictionary, 1987, McGraw–Hlll, Inc., Fifth edition, p. 291.*

* cited by examiner

Primary Examiner—Michael G. Hartley
Assistant Examiner—Sharmila S Gollamudi
(74) Attorney, Agent, or Firm—Millen, White, Zelano & Branigan, P.C.

(57) ABSTRACT

The invention relates to a pharmaceutical composition having the following constituents: azelaic acid, polyacrylic acid, triacylglyceride, propylene glycol, polysorbate, soya lecithin, water and salts. The composition is a hydrogel which is suited for the treatment of rosacea, presbyderma, melasma or skin irritations.

12 Claims, No Drawings

COMPOSITION WITH AZELAIC ACID

This application is a 371 of PCT/EP98/07370, filed Nov. 18, 1998, which claims benefit of 60/074,850, filed Feb. 12, 1998.

The invention relates to a composition with azelaic acid in a hydrogel. In addition, the use of azelaic acid-hydrogel as a pharmaceutical agent is part of the invention. This application claims the German priorities DE 197 53 044 with the application date of Nov. 19, 1997 and DE 198 08 086 with the application date of Feb. 20, 1998. The US filing of U.S. Ser. No. 60/074,850 with the filing date of Feb. 12, 1998 is claimed as an additional priority for the USA.

PRIOR ART

EP 0 336 880 A2, which was applied for on Mar. 29, 1998, describes a pharmaceutical composition that consists of (i) azelaic acid at a concentration of 20% by weight, (iii) triacylglycerides and diacylglycerides, (iv) propylene glycol, (v) polysorbate, for example polyethylene (20) sorbitan monooleate, and (vii) water and salts. This composition that is to be administered topically is used for the treatment of various age-related changes in the facial skin. The composition exists as a cream. In addition, it is known to use the azelaic acid for inflammatory and infectious dermatoses, such as, for example, acne and rosacea.

Under the number 32 282, the 1996 Red List (ISBN 3-87193-167-5) describes a pharmaceutical composition with the name Skinoren that consists of (i) azelaic acid at a concentration of 20% by weight, (iii) triacylglycerides and diacylglycerides, (iv) propylene glycol, (v) polysorbate, for example macrogol stearate 1000 and (vii) water and salts. This composition that is to be administered topically is used for the treatment of acne. The composition exists as a cream. This document is regarded as the closest prior art.

International Application WO 96/11700, which was filed on Oct. 29, 1993, describes a pharmaceutical composition that is used as an adjuvant for a vaccine. This composition is to replace the Freund adjuvant. It is injected. As a (i) pharmaceutical active ingredient, for example, hepatitis B surface protein is used. In addition, (ii) polyacrylic acid, (iii) triacylglycerides and/or diacylglycerides, such as MIGLYOL, (iv) propylene glycol, and (v) polysorbates are used in the form of TWEEN, EMULROR and SIMULSOL M-53. (vi) Soybean lecithin is also to be added. The composition is an (vii) aqueous phase with salts. The composition is not administered topically. The emulsion has particles measuring 0.03 to 0.5 μm, preferably 0.05 to 0.2 μm.

International application WO 95/05163, which was filed on Aug. 5, 1994, describes a pharmaceutical composition that exists as an emulsion for the administration of biologically active substances on the skin surface. This composition contains particles measuring 30 to 500 nm, preferably 70 to 200 nm. As (i) pharmaceutical active ingredients, for example, anti-inflammatory medications are used. In addition, (ii) polyacrylic acid, (iii) triacylglycerides and/or diacylglycerides, (iv) propylene glycol, and (v) polysorbates are used in the form of TWEEN, EMULROR, TRITON X and SIMULSOL M-53. (iv) Soybean lecithin is also to be added. The composition is an (vii) aqueous phase with salts. The composition is administered topically.

European Patent Application EP 0 696 452, which was filed on Jul. 26, 1995, describes a nanoemulsion that is used for medication for treating the eyes, whereby the nanoemulsion is administered as eye drops that are to be applied topically. This composition contains particles of a mean size of 520 nm. As (i) pharmaceutical active ingredients, for example, anti-inflammatory medications are used. In addition, (ii) polyacrylic acid, (iii) triacylglycerides and/or diacylglycerides, (iv) propylene glycol, and (v) polysorbates are used in the form of polyoxyethylene polyoxypropylene copolymers. The composition is an (vii) aqueous phase with salts. The composition is administered topically.

Object and Achievement

The object is to offer a pharmaceutical composition with azelaic acid as a therapeutic active ingredient, whereby the bioavailability of the azelaic acid is to be increased.

In a composition according to the prior art that comprises the following features:

(i) azelaic acid as a therapeutic active ingredient,
(iii) triacylglycerides,
(iv) propylene glycol, and
(v) polysorbates
(vii) in an aqueous phase that comprises water and salts, the object is achieved in that the composition comprises
(ii) polyacrylic acid, and
(vi) lecithin as other additives, and that in this case the composition is a hydrogel.

Advantages

The composition according to the invention has the advantage that it allows a larger amount of pharmaceutical active ingredient to penetrate into living skin layers and/or cutaneous organs. In this connection, the availability of the azelaic acid in the composition according to the invention is higher by a factor of three to five than in the azelaic acid-cream according to the prior art. This availability was demonstrated in a FRANZ-flow-diffusion cell test, which is depicted in detail in the examples. Specifically the living skin layers and/or cutaneous organs are the desired target sites for azelaic acid. It is especially common to use the composition in azelaic acid at high concentrations.

Another Embodiment of the Composition

A composition that is to be administered topically is advantageous.

Preferred is a composition according to the invention in which the azelaic acid is present at a concentration of 5 to 20% by weight, more preferably at a concentration of 10 to 18% by weight, and most preferably at a concentration of 14 to 16% by weight.

The presence of polyacrylic acid is essential. It is decisive for the production of the hydrogel. In the gel, the soybean lecithin is preferred as lecithin. The lecithin or soybean lecithin is advantageous at a concentration of up to 3% by weight. More preferred is a concentration of up to 1.5% by weight and most preferred a concentration of up to 1% by weight. The last concentration has the effect that the hydrogel is no longer present as a nanoemulsion.

Advantages

It has unexpectedly proven that the composition according to the invention in the case of concentrations in lecithin of 1% by weight and less does not form any standard nanoemulsion according to the prior art. Rather, a gel is present that comprises a homogenous mass with virtually no vesicles, but does have membrane fragments. The fact that azelaic acid and the remainder of the solution do not form any nanoemulsion was not expected. Only with the aid of scanning electron microscope recordings was it possible to provide clarity. It turned out that no nanoemulsion could be identified in microscopic examination. Advantageously, the composition according to the invention has a high penetration in living skin layers and/or cutaneous organs, which cannot be observed in creams.

Preferred Embodiments

Preferred is a composition in which the individual parameters, independently of one another, can have the following concentrations:
- (ii) Polyacrylic acid at a concentration of 0.5 to 2% by weight,
- (iii) triacylglycerides at a concentration of 0.5 to 5% by weight,
- (iv) propylene glycol at a concentration of 5 to 15% by weight, and
- (v) polysorbates at a concentration of 0.5 to 3% by weight.

The components are to be adapted to one another, of course, so that a sum of 100% is achieved.

Most preferred is a composition in which the individual parameters, independently of one another, can have the following concentrations:
- (ii) Polyacrylic acid at a concentration of 1±0.25% by weight,
- (iii) triacylglycerides at a concentration of 2±1% by weight,
- (iv) propylene glycol at a concentration of 10±2% by weight, and
- (v) polysorbates at a concentration of 2±0.5% by weight.

The components are to be adapted to one another, of course, so that a sum of 100% is achieved.

Definitions

Azelaic acid and its production is described in German Patent DE 28 17 133.7. Cf. Römpp, Chemie Lexikon [Lexicon of Chemistry], issued by Jürgen FALBE and Manfred REGNITZ, 1989, 9th Edition, page 323, Thieme Verlag Stuttgart, ISBN 3-13-734609-6.

Polyacrylic acid represents an anion-active polymerizate of acrylic acid, which is only partially water-soluble. The one-percent aqueous suspension has a pH of 3 and approximately the same viscosity as water. It is only during neutralization with inorganic or organic bases that gel formation and the production of highly viscous products take place. Rudolf VOIGT and Manfred BORNSCHEIN, 1979, Lehrbuch der pharmazeutischen Technologie [Textbook of Pharmaceutical Technology], page 314, VEB Verlag Volk und Gesundheit Berlin. Cf. Römpp, Chemie Lexikon, issued by Jürgen FALBE and Manfred REGNITZ, 1992, 9th Edition, page 3508, Thieme Verlag Stuttgart, ISBN 3-13-735009-3.

"Triglyceride" is a designation for esters of the glycerine whose three hydrogen groups are esterified by carboxylic acids. The naturally occurring fats and fatty oils are triglycerides ("neutral fats"), which generally contain various fatty acids in the same glycerine molecule. J. Am.-Oil. Chem Soc. Vol. 62, page 730, (1985); and Parfüm, Kosmet. [Perfume, Cosmet.], Vol. 58, page 353, (1977); and Römpp, Chemie Lexikon, issued by Jürgen FALBE and Manfred REGNITZ, 1990, 9th Edition, pages 1339–1342, Thieme Verlag Stuttgart, ISBN 3-13-734709-2.

Propylene glycol is described in H. P. FIEDLER: Lexikon der Hilfsstoffe [Lexicon of Adjuvants], 4th Edition, 1996, ISBN 3-87193-173 on pages 1278 to 1282.

Polysorbates are described in H. P. FIEDLER: Lexikon der Hilfsstoffe, 4th Edition, 1996, ISBN 3-87193-173 on pages 1251 to 1252.

Lecithins are obtained by extraction from biological material. A lecithin fraction from soybeans (the most common raw material) thus comprises, e.g., palmitic acid, stearic acid, palmitoleic acid, oleic acid, linoleic acid and linolenic acid. Normally, the saturated fatty acid with the primary hydroxy group of the glycerine and the unsaturated fatty acid with the secondary hydroxy group of the glycerine are esterified. Lecithins are components of cell membranes of all living creatures. In water, lecithins first swell up like lyophilic colloids. Later, they produce transparent, colloidal solutions. Depending on water content, they form different textures, whereby the lamellae are formed from lipid-double layers. Liposomes are produced at higher water content. Lit.: Pardun, Die Pflanzenlecithine [The Plant Lecithins], Augsburg: Verl. für Chem. Ind. (Ziolkowsky KG) 1988. Other lecithins and their action are described in J. GAREISS et al. 1994, Parfümerie und Kosmetik [Perfumes and Cosmetics], Vol. 10/94, pages 652–659, Hüthing GmbH Heidelberg.

A gel is distinguished by the following properties: it is a dimensionally stable, easily deformable, liquid and optionally gas-rich, dispersed system that consists of at least two components. Römpp, Chemie Lexikon, issued by Jürgen FALBE and Manfred REGNITZ, 1990, 9th Edition, page 1511, Thieme Verlag Stuttgart, ISBN 3-13-734709-2; and Pharm. Unserer Zeit, Vol. 8, pages 179-to 188, (1979): and Parfüm., Kosmet., Vol. 58, pages 251 to 253 (1977).

Preservatives can be contained in the aqueous phase. Preservatives include, for example, benzoic acid. Based on its antimicrobial property, benzoic acid is especially suitable as a preservative.

Properties When Used as a Medication

The composition of the invention shows pharmacological action and can be used as a therapeutic active ingredient or as a medication.

Preferred is a composition according to the invention together with at least one physiologically compatible, pharmacological adjuvant or vehicle. Pharmacological adjuvants and vehicles are described in Remington's Pharmaceutical Science, 15th Edition, Mack Publishing Company, Easton, Pa. (1980).

The composition of the invention is suitable for the treatment of various indications. Preferred is a composition of the invention as a therapeutic active ingredient for treating rosacea, presbyderma, melasma, acne and/or skin irritations. More preferred is a composition of the invention as a therapeutic active ingredient for treating rosacea, presbyderma, melasma, acne and/or skin irritations together with at least one physiologically compatible, pharmacological adjuvant or vehicle. The treatment comprises prophylactic and therapeutic measures.

(i) In addition, the invention provides
- (α) the use of the pharmaceutical composition of the invention for the production of a medication for treating rosacea, presbyderma, melasma, acne and/or skin irritations;
- (β) a process for treating rosacea, presbyderma, melasma, acne and/or skin irritations, said process comprises an administration of a pharmaceutical composition according to the invention, whereby the amount suppresses the disease, and whereby the pharmaceutical composition is given to a patient who requires such a medication;

(γ) a pharmaceutical composition for treating rosacea, presbyderma, melasma, acne and/or skin irritations, said treatment comprises a pharmaceutical composition of the invention and at least one pharmaceutically compatible vehicle and additive.

For these therapeutic actions, the suitable dose is different and depends on, for example, the concentration of the individual elements in the pharmaceutical composition, the host, the type of administration and the type and severity of the conditions to be treated.

In the case of topical treatment, the pharmaceutical composition of the invention can be administered in any usual way. Gel is preferred.

The pharmaceutical composition of the invention can be administered in the usual topical methods of administration with the additives and/or vehicles that are commonly used in galenical pharmaceutics according to methods that are known in the art.

EXAMPLES

1. Production of the Pharmaceutical Composition

A pharmaceutical composition that contains azelaic acid has the following formulation and the following process steps:

Benzoic acid and EDTA are dissolved in usual concentrations in 60 to 70 parts of water. Then, a mixture of 1 part of mid-chain triglycerides and 1.5 parts of polysorbate 80 is to be added and homogenized while being stirred (pre-emulsion). One part of lecithin is introduced into 12 parts of propylene glycol. The solution that is produced is stirred into the pre-emulsion and homogenized. After 1 part of polyacrylic acid is added, 15 parts of azelaic acid are introduced into the pharmaceutical composition that is produced. Then, the orientation of the gel former is carried out with the necessary amount of sodium hydroxide solution. The resulting gel has an approximately 4-times higher availability of azelaic acid in living skin layers and/or cutaneous organs.

2. Detection of Bioavailability in the Skin

The percutaneous resorption of azelaic acid was examined from hydrogel formulations according to the invention in comparison to Skinoren$^{(R)}$ cream. The purpose of the study was to describe the bioavailability of azelaic acid in the skin, the penetration of azelaic acid through the skin and the dermal metabolism of azelaic acid. In this respect, various preparations that contain $^{14}$C-labeled azelaic acid were applied in the in vitro model of the FRANZ diffusion chamber on the intact complete skin of hairless mice (MF1 hr/hr Ola/Hsd; supplier: Winkelmann, Germany). An amount of 10 to 15 mg of the following compositions was applied to a skin area of 2 cm$^2$:

A) 20% azelaic acid in a cream whose adjuvant composition corresponds to that of Skinoren$^{(R)}$ cream, B) 15% azelaic acid in a composition according to the invention.

The time behavior of the $^{14}$C-azelaic acid was measured in the acceptor medium (Hepes Hanks Balanced Salt Solution: HHBSS), which flows along under the skin, at two-hour intervals over a period of 24 hours. In addition, at the end of each experiment, the radioactivity on the skin surface, in the stratum corneum and in the remaining skin was determined. To study the metabolism of azelaic acid in the skin, skin extracts and selected fractions of the acceptor medium were examined using radiochromatography (HPLC and radiometric detection).

The $^{14}$C-azelaic acid found in the skin at the end of the experiment was metabolized only to a proportion of 3 to 11%. Therefore, the data on the radioactivity in the skin can virtually be equated to the concentration of unchanged azelaic acid.

The following table contains a summary of the results:

|  | Cream According to the Prior Art | | Composition According to the Invention | |
|---|---|---|---|---|
|  | Mean | SD | Mean | SD |
| Not [one word non-penetrated azelaic acid | 79.9% | 14.3% | 63.6% | 20.6% |
| Azelaic acid in the stratum corneum | 0.9% | 0.7% | 4.0% | 1.9% |
| Azelaic acid in the remaining skin | 3.7% | 2.0% | 27.3% | 17.1% |
| Azelaic acid in the acceptor medium | 16.3% | 6.3% | 5.8% | 3.3% |

SD = standard deviation

In comparison to the standard cream, considerably higher azelaic acid concentrations in the skin were achieved with the agent according to the invention.

What is claimed is:

1. A composition that comprises:
   (i) azelaic acid as a therapeutically active ingredient in a concentration of 5 to 20% by weight,
   (iii) at least one triacylglyceride in a concentration of 0.5 to 5% by weight,
   (iv) propylene glycol, and
   (v) at least one polysorbate, in an aqueous phase that further comprises water and salts, and the composition further comprises
   (ii) at least one polyacrylic acid, and
   (vi) lecithin,
   wherein the composition is in the form of a hydrogel.

2. A composition according to claim 1, wherein the composition is in a form for topical administration.

3. A composition according to claim 1, wherein the lecithin is soybean lecithin.

4. A composition according to claim 1, wherein the lecithin is present at a concentration within the range of greater than 0% to 1% by weight.

5. A composition according to claim 1, wherein the individual components, independently of one another, have the following concentrations;
   (ii) at least one polyacrylic acid at a concentration of 0.5 to 2% by weight,
   (iii) at least one triacylglyceride at a concentration of 0.5 to 5% by weight,
   (iv) propylene glycol at a concentration of 5 to 15% by weight, and
   (v) at least one polysorbate at a concentration of 0.5 to 3% by weight.

6. A composition according to claim 1, wherein the individual components, independently of one another, have the following concentrations:
   (ii) at least one polyacrylic acid at a concentration of 1±0.25% by weight,
   (iii) at least one triacylglyceride at a concentration of 2±1% by weight,
   (iv) propylene glycol at a concentration of 10±2-% by weight, and (v) at least one polysorbate at a concentration of 2±0.5% by weight.

7. A composition according to claim 1, wherein the composition further comprises at least one physiologically compatible, pharmacological adjuvant or vehicle.

8. A method for treating rosacea, presbyderma, melasma, acne and/or skin irritations in a patient, comprising administering to the patient in need thereof a therapeutically effective amount of the composition according to claim 1.

9. The method of claim 8, wherein the composition is administered topically.

10. A composition according to claim 1, wherein the azelaic acid is present at a concentration of 10 to 18% by weight.

11. A composition according to claim 1, wherein the lecithin is present at a concentration within the range of greater than 0% to 3% by weight.

12. A composition according to claim 1, further comprising benzoic acid.

* * * * *